United States Patent [19]

Baserga

[11] 4,009,189
[45] Feb. 22, 1977

[54] BASIC ANTHRAQUINONE DYES, THEIR PRODUCTION AND USE

[75] Inventor: Emilio Baserga, Zurich, Switzerland

[73] Assignee: Sandoz Ltd., Basel, Switzerland

[22] Filed: June 9, 1975

[21] Appl. No.: 584,814

Related U.S. Application Data

[63] Continuation of Ser. No. 357,114, May 4, 1973, abandoned, which is a continuation of Ser. No. 32,381, April 27, 1970, abandoned.

[30] Foreign Application Priority Data

May 21, 1969 Switzerland .................. 7690/69
June 6, 1969 Switzerland .................. 8646/69

[52] U.S. Cl. .................. 260/381; 8/39 A
[51] Int. Cl.² ............... C07C 97/25; C09B 1/16
[58] Field of Search .................. 260/381

[56] References Cited

UNITED STATES PATENTS

| | | | |
|---|---|---|---|
| 2,226,909 | 12/1940 | Peter | 260/381 X |
| 2,487,045 | 11/1949 | Dickey et al. | 260/381 X |
| 2,716,655 | 8/1955 | Boyd | 260/381 |
| 3,123,605 | 3/1964 | Turetzky et al. | 260/381 X |
| 3,657,284 | 4/1972 | Booth et al. | 260/381 X |
| 3,882,150 | 5/1975 | Frey et al. | 260/381 X |

Primary Examiner—Paul F. Shaver
Attorney, Agent, or Firm—Gerald D. Sharkin; Richard E. Vila; Thomas C. Doyle

[57] ABSTRACT

Basic 4-alkylaminoanthraquinone dyes which bear a non-water-solubilizing substituent in the 2-position and in which the alkyl side-chain in the α-position to the anthraquinoneamino group is branched, which are useful for the exhaustion dyeing, pad dyeing and printing of textiles which consist wholly or partly of a polyacrylonitrile or acrylonitrile copolymer fiber.

8 Claims, No Drawings

BASIC ANTHRAQUINONE DYES, THEIR PRODUCTION AND USE

This is a continuation of application Ser. No. 357,114, filed May 4, 1973 which in turn is a continuation of application No. 32,381, filed Apr. 27, 1970, both now abandoned.

This invention is directed to basic 4-alkylaminoanthraquinone dyes which bear a non-water-solubilizing substituent in the 2-position and in which the alkyl side-chain in the α-position to the anthraquinoneamino group is branched. These dyes are used for the exhaustion dyeing, pad dyeing and printing of textiles which consist wholly or partly of a polyacrylonitrile or acrylonitrile copolymer fibre, on which fibres they give dyeings and prints of superior light fastness.

The invention thus relates to a process for the exhaustion dyeing, pad dyeing and printing of textiles which are composed of, or contain, a polyacrylonitrile or acrylonitrile copolymer fibre, with basic dyes of the anthraquinone series, which process is characterized in that dyes free from sulphonic acid groups are employed which are of formula

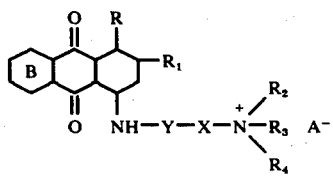

(I).

In formula (I)

R stands for the hydroxyl group or a group of formula —$NHR_5$, $R_1$ for a non-water-solubilizing substituent, $R_2$ and $R_3$ each stands for a hydrocarbon radical which may be substituted, $R_4$ for a hydrogen atom or an alkyl or phenyl radical which may be substituted, Y for a group of formula

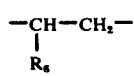

or for a divalent, saturated or partially saturated ring system which may be substituted, X for the direct linkage or a divalent bridge member, $R_5$ for hydrogen or a hydrocarbon radical which may be substituted, $R_6$ for a hydrocarbon radical which may be substituted, and $A^-$ for an anion.

In this formula the ring B may be further substituted and the radicals $R_2$ and $R_3$ or the radicals $R_2$, $R_3$ and $R_4$ jointly with the $N^+$ atom may form a ring.

This invention relates further to new basic anthraquinone dyes, likewise free from sulphonic acid groups, which are of formula

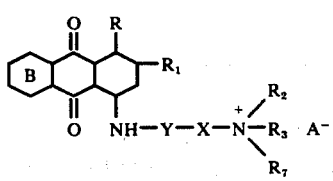

(II), where R, $R_1$, $R_2$, $R_3$, B, X, Y and $A^-$ have the aforestated meanings and $R_7$ represents an alkyl or phenyl radical which may be substituted;

the radicals $R_2$ and $R_3$ or the radicals $R_2$, $R_3$ and $R_7$ together with the $N^+$ atom may form a ring.

Generally $R_1$ represents halogen, preferably chlorine or bromine; (dyes of formula III).

Dyes of good quality are those of formula

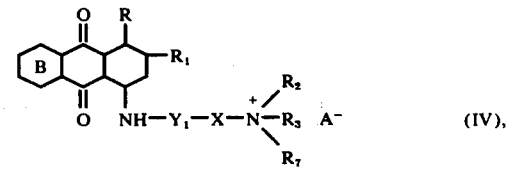

(IV), where $Y_1$ stands for a group of formula

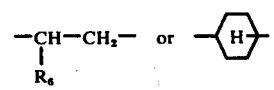

and the cycloaliphatic ring H may bear further substituents, and where $R_1$ is preferably a halogen atom, more especially a chlorine or bromine atom.

Dyes of similarly good quality have the formula

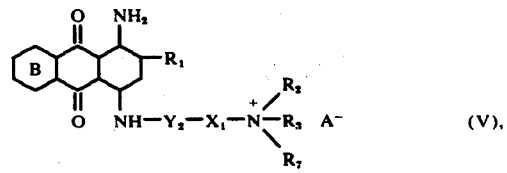

(V), where $R_1$ stands for chlorine or bromine, $Y_2$ for a group of formula

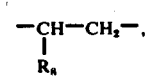

$X_1$ for the direct linkage or —$CH_2$—, —$C_2H_4$—or —$OC_2H_4$—and $R_8$ for —$CH_3$, —$C_2H_5$, —$C_3H_7$,

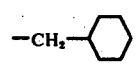

or 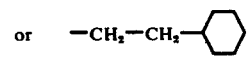

The new dyes of formula (II) can be produced by reacting a compound of formula

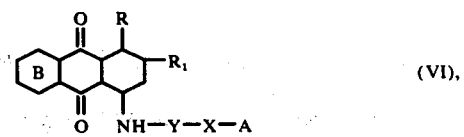

(VI), where A represents a radical convertible into an anion $A^-$, with an amine of formula

Alternatively the dyes of formula (II) can be synthesized by reacting a compound of formula

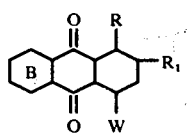

where W represents a substituent which reacts with an amino group, with a compound of formula

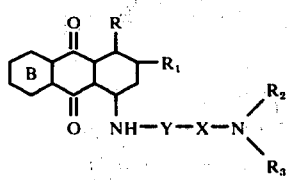

Another method of formation for the dyes of formula (II) is to react a compound of formula

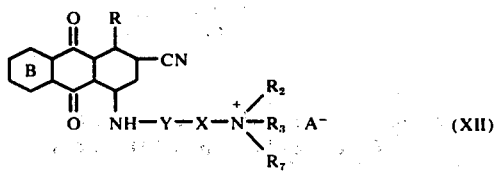

with a quaternating agent, for example a compound of formula $$R_7 - A \quad (XI).$$

The dyes of formula

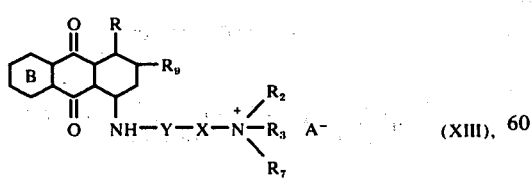

can be produced by treatment of a compound of formula

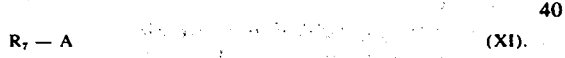

where $R_9$ represents halogen or the $-SO_3H$ group, with an alkali cyanide.

The present invention relates further to other new anthraquinone dyes free from sulphonic acid groups which are of formula

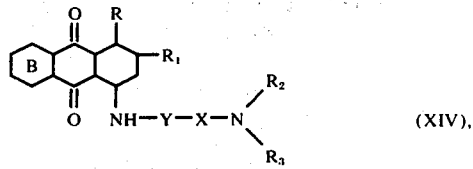

where R, $R_1$, $R_2$, $R_3$, B, X and Y have the meanings given in the foregoing and $R_2$ and $R_3$, jointly with the N atom attached thereto, may form a ring. Again in formula (XIV) $R_1$ stands primarily for halogen and preferably for chlorine or bromine; (dyes of formula XV).

A group of good dyes are those of formula

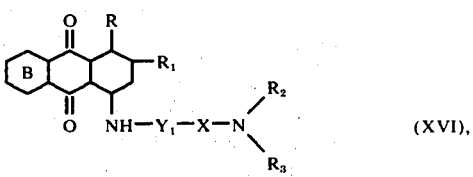

where $Y_1$ represents a group of formula

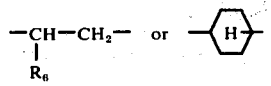

and where the cycloaliphatic ring H may be further substituted and $R_1$ stands advantageously for a halogen atom, preferably for a chlorine or bromine atom.

Comparably good dyes are of formula

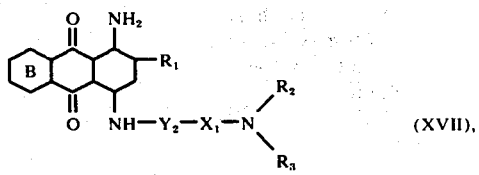

where
$R_1$ stands for chlorine or bromine,
$Y_2$ for a group of formula

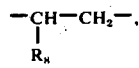

$X_1$ for the direct linkage or $CH_2-$, $-C_2H_4-$ or $-OC_2H_4-$
and
$R_8$ for $-CH_3$, $-C_2H_5$, $-C_3H_7$,

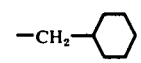

or 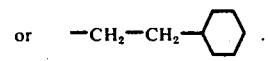

The dyes of formula (XIV) can be produced by reacting a compound of formula (VIII) with an amine of formula

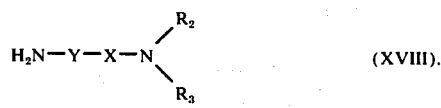 (XVIII).

A second route of synthesis for the dyes of formula (XIV) is to react a compound of formula (VI), where A represents the acid radical of an ester, with an amine of formula

 (XIX).

The dyes of formula

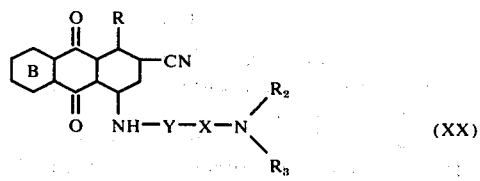 (XX)

can be formed by treating with an alkali cyanide a compound of formula

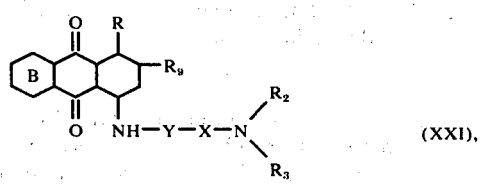 (XXI), where $R_9$ stands for halogen or the —$SO_3H$ group. Examples of suitable hydrocarbon radicals are optionally substituted alkyl radicals such as cycloalkyl radicals, e.g. cyclohexyl and alkylcyclohexyl radicals, and optionally substituted aryl radicals such as phenyl and naphthyl radicals.

The alkyl radicals, including those which are straight or branched, generally contain 1 to 12, preferably 1 to 6 or more specifically 1, 2, 3 or 4 carbon atoms. If these radicals are substituted they contain in particular halogen atoms, hydroxyl or cyano groups and aryl radicals such as phenyl radicals; in such cases alkyl stands for an aralkyl radical such as a benzyl radical. The alkoxy may bear 1 to 6 or preferably 1, 2 or 3 carbon atoms. The non-water-solubilizing substituents $R_1$ may be, for example, halogen atoms, nitro, primary, secondary or tertiary amino, cyano, thiocyano, hydroxyl, alkyl, alkoxy, trifluoralkyl, trichloralkyl, phenyl, phenyloxy, alkylamino, dialkylamino or phenylamino groups; in no instance does $R_1$ represent hydrogen. The aforenamed substitutents may occur generally in the other radicals of aromatic character, e.g. in the ring B, or in phenyl or naphthyl radicals.

The divalent bridge members may be substituted or unsubstituted alkylene or alkenylene radicals having 1 to 12 or preferably 1 to 6 carbon atoms; these radicals may be branched or bound to members of a ring system such as cyclohexylene or phenylene radicals or to hetero atoms or groups of hetero atoms, or they may be interrupted by such groups, e.g. by -O-, -S-,

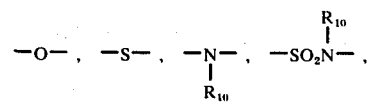

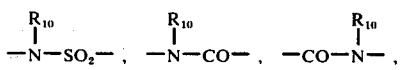

where $R_{10}$ represents a hydrogen atom or an unsubstituted or substituted hydrocarbon radical.

Examples of the bridge members X are —$(CH_2)_p$— where p has the numerical significance of 1 to 6, —$CH_2$—$CH$—$CH_3$, —$NH$—$CH_2$—$CHOH$—$CH_2$—, —$CH_2$—$CHOH$—$CH_2$—, —$CH_2$—$CO$—$NH$—$CH_2$—, —$CH_2$—$NH$—$CO$—$CH_2$—,

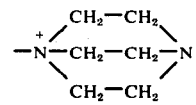

etc.

The radicals $R_2$ and $R_3$, jointly with the vicinal $N^+$ atom or with the N atom, may form a heterocycle such as a pyrrolidine, piperidine, morpholine, aziridine or piperazine ring.

The radicals $R_2$, $R_3$ and $R_4$ or $R_7$, together with the neighbouring $N^+$ atom, may form a heterocycle, e.g. a group of formula

or may stand for a pyridinium ring.

The preferred radicals A are those of hydrohalic acids; A stands preferably for chlorine or bromine. Examples of other suitable radicals A are the radicals of sulphuric acid, of a sulphonic acid and of hydrogen sulphide.

The hydroxyl group, an amino or alkoxy group and halogen atoms may be named to exemplify the substituents which react with amino groups.

In every instance halogen is understood to mean chlorine, bromine, fluorine or iodine.

The anion $A^-$ in the compounds of formulae (I) and (II) can be exchanged for a different anion by means of an ion exchanger or by reaction with salts or acids, if necessary in more than one step, e.g. via the hydroxide or the bicarbonate.

The anion $A^-$ may be an organic or inorganic ion. Examples are halogen ions such as those of chloride, bromide or iodide, the ions of sulphate, disulphate, methylsulphate, aminosulphonate, perchlorate, carbonate, bicarbonate, phosphate, phosphorus molybdate, phosphorus tungstate, phosphorus tungstic molybdate, benzenesulphonate, naphthalenesulphonate, 4-chlorobenzenesulphonate, oxalate, maleinate, acetate, propionate, lactate, succinate, chloracetate, tartrate, methanesulphonate and benzoate; complex anions also can be employed, such as that of zinc chloride double salts.

Suitable quaternating agents include alkyl halides such as methyl and ethyl chloride, bromide and iodide, alkylsulphates such as dimethylsulphate, benzyl chloride, acrylic amides/hydrochloride, e.g. $CH_2=CH-CO-NH_2/HCl$, chloracetic acid alkylester, β-chloropropionic amide, epoxides such as ethylene oxide, propylene oxide, epichlorohydrin.

Quaternation can be effected by any of the known methods, e.g. in an inert solvent, in aqueous suspension, or in an excess of the quaternating agent in the absence of solvent, if necessary at high temperatures and in buffered medium. It is of advantage to use organic acids, in conjunction with a basic compound as required. The reaction of a compound of formula (VI) with an amine of formula (VII) or (XIX) can likewise be carried out by known methods, e.g. in an organic solvent at temperatures of −50° C to +250° C, preferably in the range of −10° C to +120 ° C.

A compound of formula (VIII) can be reacted with an amine of formula (IX) or (XVIII) by any of the known methods, e.g. in aqueous solution, in an organic solvent or in a mixture of water and an organic solvent, if necessary in the presence of a buffer solution and at high temperatures, preferably at the boiling point of the solvent used. On completion of this reaction the compound formed is normally present in the leuco form and is subsequently oxidized, for example by directing a jet of air into the reaction mixture.

Similarly, the reaction of compounds of formulae (XIII) and (XXI) with an alkali cyanide can be conducted according to the normal methods, e.g. in water or an organic solvent, if necessary in the presence of a buffer and at high temperatures. In many cases this reaction too yields leuco compounds which have to be oxidized.

The new dyes of formula (I) are used primarily for the exhaustion dyeing, pad dyeing and printing of polyacrylonitrile and acrylonitrile copolymer fibres and the textiles fabricated wholly or in part with these fibres; that is to say, the dyes can be applied to these fibres in loose form, as yarn or in any of the later stages of manufacture. The new dyes are also suitable for the exhaustion dyeing, pad dyeing and printing of polyamide and polyester fibres modified by the introduction of acid groups. Polyamide fibres of this type are described in Belgian Pat. No 706,104 and the corresponding polyester fibres in U.S. Pat. Nos. 3,018,272 and 3,379,723.

The dyes are normally applied from an aqueous medium of neutral or acid reaction in the temperature range of 50° or 60° C to 100° C, or alternatively at temperatures above 100° C under static pressure. Level dyeings are obtained without the use of retarders. The component of polyacrylonitrile or acrylonitrile copolymer fibre in blends can be successfully dyed with these new dyes. The dyes of this invention which are well soluble in organic solvents can be employed for the coloration of natural and synthetic resins and plastics in the dissolved or undissolved state. It has been found that mixtures of two or more of these dyes or mixtures with other cationic dyes are well compatible and can be used with good success. The dyes have further uses for the dyeing of leather and paper.

On polyacrylonitrile and acrylonitrile copolymer fibres level dyeings are obtained which have good fastness to light and wet treatments such as washing, perspiration, water, sea water and cross dyeing, together with good fastness to sublimation and pleating. The dye of formula

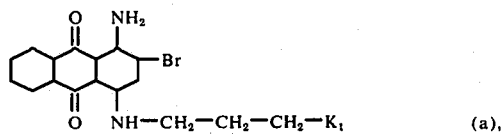

(a), where $K_1$ represents a group of formula $-N(CH_3)_2$ or $-N^+(CH_3)_3 \cdot CH_3SO_4^-$ is known from U.S. Pat. No. 2,716,655 to be suitable for dyeing polyacrylonitrile and acrylonitrile copolymer fibers. It is surprising that the dyes of formula (I) are faster to light than this dye on the said fibres.

In the following Examples the parts and percentages are by weight and the temperatures are given in degrees centigrade.

Example 1

43.7 Parts of 1-amino-2-bromo-4-(2'-β-chlorethoxy-1'-methyl)ethylaminoanthraquinone are dissolved in 120 parts of pyridine at 100°. The solution is stirred for 4 hours at 100°–100°, on which the pyridinium dye formed settles out. Stirring is continued till the mixture is cold, then the precipitate is filtered off with suction, washed with cold methanol and dried at 60° with vacuum.

This dye is applied to polyacrylonitrile fibres from acetic acid solution to give dyeings of brilliant reddish blue shade having good light fastness.

Example 2

28.5 Parts of the compound formed by condensation of 1-amino-4-bromanthraquinone-2-sulphonic acid and 4-aminocyclohexyltrimethylammonium-methylsulphate are entered into 180 parts of water. The temperature is increased to 80°, 20 parts of monosodium phosphate and 15 parts of sodium bicarbonate are added and the reaction mixture is stirred for 12 to 15 hours at 80°–85° C. As formed, the resulting dye is partly in the leuco form, so air is blown into the reaction mixture at 80° for oxidation. The dye is then salted out, filtered off with suction, washed with dilute common salt solution and dried at 60°.

Example 3

44.6 Parts of 1-amino-2-bromo-4-(2'-β-dimethylaminoethoxy-1'-methyl)-ethylaminoanthraquinone are dissolved in 500 parts of chlorobenzene at 60°, with the subsequent addition over 2 hours of 15 parts of dimethyl sulphate. The suspension thus formed is stirred for 2 hours at 60°, on which the dye settles out. It is filtered off with suction, washed with chlorobenzene until the washing liquid runs off clear, and dried at 60° with vacuum.

Dyed from acetic acid solution, this dye gives brilliant reddish blue dyeings on polyacrylonitrile fibres which have excellent light fastness.

Example 4

A suspension of 31.6 parts of 1-amino-4-bromo-2-methylanthraquinone, 0.5 part of copper acetate, 10 parts of potassium acetate and 30 parts of 2-aminopropyltrimethylammonium-methyl sulphate in 300 parts of ethyl alcohol is stirred for 14 hours at 78°. The dye thus formed is isolated by one of the known methods. It gives dyeings of violet blue shade on polyacrylonitrile fibres which have good fastness properties, the light fastness being particularly good.

Dyeing Example A

A mixture of 20 parts of the dye of Example 1 and 80 parts of dextrin is ground in a ball mill for 48 hours. One part of the resulting preparation is pasted with 40% acetic acid and 400 parts of distilled water at 60° are poured onto the paste with constant agitation. After boiling for a short time to dissolve, the solution is diluted with 7600 parts of distilled water and 2 parts of glacial acetic acid are added. 100 Parts of a fabric of polyacrylonitrile fibre, previously treated for 10–15 minutes at 60° in a bath of 8000 parts of water and 2 parts of glacial acetic acid, are entered into the dyebath at 60°. The temperature is increased to 100° in 30 minutes and the fabric dyed at this temperature for 1 hour. On removal it is raised and dried. A level dyeing of reddish blue shade is obtained which has excellent light fastness and very good wet fastness properties.

Example 5

A suspension of 38.1 parts of 1-amino-2,4-dibromoanthraquinone, 17 parts of 3-amino-1-dimethylaminobutane, 10 parts of potassium acetate and 0.5 parts of copper acetate in 130 parts of n-butanol is stirred at 100° until the chromatogram of a sample shows that no further 1-amino-2,4-dibromoanthraquinone is present. In the course of the reaction the blue dye formed goes into solution, which permits the precipitated by-products and inorganic salts to be filtered off at 80°. The residue is washed with 20 parts of n-butanol at 60°. The volume of the mother liquor is reduced by partial evaporation and after it has cooled the dye settles out in crystalline form. It dyes polyacrylonitrile fibres in reddish blue shades which have good light and wet fastness properties.

Example 6

22 Parts of 1-amino-4-(4'-dimethylamino)-cyclohexylaminoanthraquinone-2-sulphonic acid are dissolved in 500 parts of water at 60°, with the addition of 5 parts of sodium bicarbonate. 7.5 parts of sodium cyanide are added and the solution is stirred for 10 hours at 80°–85°. In the course of the next 3 hours at a temperature of 80° air is injected into the mixture to oxidize the proportion of the product which is present in the leuco form. Subsequently the precipitated dye is filtered off with suction, washed with water until neutral and dried.

Example 7

20 Parts of 1-amino-2-bromo-4-(2'-β-chlorethoxy-1'-methyl)ethylaminoanthraquinone are dissolved in 200 parts of benzene and 10 parts of diethylamine are added to the solution. It is maintained at 60° until chromatography of a sample reveals that no further starting product is present. Hydrogen chloride gas is conducted into the solution to cause precipitation of the hydrochloride of 1-amino-2-bromo-4-(2'-β-diethylaminoethoxy-1'-methyl)-ethylaminoanthraquinone. This is filtered off with suction, washed with benzene and dried at 60°.

Dyeing Example B

A mixture of 20 parts of the dye of Example 5 and 80 parts of dextrin is ground in a ball mill for 48 hours. One part of the resulting preparation is pasted with 40% acetic acid and 400 parts of distilled water at 60° are poured over the paste with constant agitation, after which the whole is boiled for a short time to dissolve. The solution is diluted with 7600 parts of distilled water and 2 parts of glacial acetic acid are added. 100 Parts of a polyacrylonitrile fabric, previously treated for 10–15 minutes at 60° in a bath of 8000 parts of water and 2 parts of glacial acetic acid, are entered into the dyebath at 60°. The bath is raised to 100° in 30 minutes, the fabric dyed for one hour at this temperature and subsequently rinsed. A level reddish blue dyeing is obtained which has excellent light fastness and very good wet fastness properties.

The following Table I shows the structural composition of further dyes which can be produced in accordance with the procedures of Examples 5 to 7. These dyes have the formula

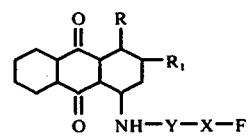

in which R, $R_1$, X, Y and F bear the meanings assigned to them in the table. The F symbol may denote any one of the radicals F listed in Table (a). These groupings can be exchanged for another of the given groupings in any particular dye.

Table (a)

F may represent any one of the symbols $F_1$ to $F_{10}$, which signify the groupings listed below:

Table (a)

| | | |
|---|---|---|
| $F_1$ | represents | $-N(CH_3)_2$ |
| $F_2$ | " | $-N(C_2H_5)_2$ |
| $F_3$ | " | $-N\begin{smallmatrix}CH_3\\C_2H_5\end{smallmatrix}$ |
| $F_4$ | " | $-N\begin{smallmatrix}CH_3\\\phantom{x}\end{smallmatrix}$ (with phenyl-H) |
| $F_5$ | " | $-N$ (piperidinyl) |
| $F_6$ | " | $-N$ (pyrrolidinyl) |
| $F_7$ | " | $-N\phantom{x}O$ (morpholinyl) |
| $F_8$ | " | $-N\begin{smallmatrix}CH_3\\C_2H_4OH\end{smallmatrix}$ |

Table (a)-continued

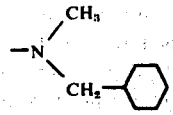

| | | |
|---|---|---|
| F₁₀ | " | —N(C₂H₄OH)₂ |

Table 1

| Example No | R | R₁ | F | Y | X | Shade of dyeing on Polyacrylo-nitrile fibre |
|---|---|---|---|---|---|---|
| 8 | OH | Cl | F₁ | CH₃<br>\|<br>—CH—CH₂— | direct linkage | red violet |
| 9 | " | Br | F₂ | " | " | " |
| 10 | " | " | F₁ | —⟨H⟩— | " | violet |
| 11 | " | " | F₂ | CH₃<br>\|<br>—CH—CH₂— | —CH₂— | " |
| 12 | " | " | F₁ | " | —OCH₂CH₂— | " |
| 13 | NHCH₃ | " | " | " | " | greenish blue |
| 14 | NH₂ | CH₃ | " | " | " | reddish blue |
| 15 | " | " | F₂ | " | " | " |
| 16 | " | " | F₃ | " | —CH₂— | " |
| 17 | " | " | F₁ | CH₂—⟨ ⟩<br>\|<br>—CH—CH₂— | " | " |
| 18 | " | " | F₂ | —⟨H⟩— | direct linkage | " |
| 19 | " | " | F₁ | " | " | " |
| 20 | " | " | " | CH₂—CH₃<br>\|<br>—CH—CH₂— | " | " |
| 21 | " | " | F₂ | " | " | " |
| 22 | " | " | F₁ | CH₃<br>\|<br>—CH—CH₂— | —CH₂—CH₂— | " |
| 23 | " | " | F₂ | " | " | " |
| 24 | " | CN | F₁ | " | " | blue |
| 25 | " | " | F₂ | " | " | " |
| 26 | " | " | F₃ | " | —OCH₂CH₂— | " |
| 27 | " | " | F₁₀ | " | " | " |
| 28 | " | Br | F₁ | " | direct linkage | reddish blue |
| 29 | " | " | F₂ | " | " | " |
| 30 | " | " | F₃ | " | " | " |
| 31 | " | " | F₂ | " | —CH₂— | blue |
| 32 | " | " | F₃ | " | " | " |
| 33 | " | " | F₄ | " | " | " |
| 34 | " | Br | F₅ | " | direct linkage | " |
| 35 | " | " | F₆ | " | " | " |
| 36 | " | " | F₇ | " | " | " |
| 37 | " | " | F₈ | " | " | " |
| 38 | " | " | F₉ | " | " | " |
| 39 | " | " | F₁₀ | " | " | " |
| 40 | " | " | F₁ | " | —CH₂—CH₂— | " |

Table 1-continued

| Example No | R | R₁ | F | Y | X | Shade of dyeing on Polyacrylonitrile fibre |
|---|---|---|---|---|---|---|
| 41 | " | " | $F_2$ | " | " | " |
| 42 | " | " | $F_1$ | " | $-OCH_2-CH_2-$ | " |
| 43 | " | " | $F_3$ | " | " | " |
| 44 | " | " | $F_4$ | " | " | " |
| 45 | " | " | $F_{10}$ | " | " | " |
| 46 | " | " | $F_2$ | $\underset{\underset{-CH-CH_2-}{\mid}}{C_2H_5}$ | direct linkage | reddish blue |
| 47 | " | " | $F_5$ | " | " | " |
| 48 | " | " | $F_7$ | " | " | " |
| 49 | " | " | $F_1$ | $\underset{\underset{-CH-CH_2-}{\mid}}{C_3H_7}$ | " | " |
| 50 | " | " | $F_2$ | " | " | " |
| 51 | " | " | $F_4$ | $\underset{\underset{-CH-CH_2-}{\mid}}{CH_2-\bigcirc}$ | $-CH_2-$ | blue |
| 52 | " | " | $F_{10}$ | " | " | " |
| 53 | " | " | $F_1$ | $\underset{\underset{-CH-CH_2-}{\mid}}{C_2H_4-\bigcirc}$ | " | " |
| 54 | " | " | $F_1$ | $-\bigcirc_H-$ | direct linkage | " |
| 55 | " | " | $F_2$ | " | " | " |
| 56 | " | " | $F_1$ | $\underset{\underset{-CH-CH_2-}{\mid}}{C_2H_5}$ | $-CH_2-$ | " |
| 57 | " | " | $F_4$ | " | " | " |
| 58 | " | $-OC_2H_5$ | $F_1$ | " | " | violet |
| 59 | " | " | $F_7$ | $-\bigcirc_H-$ | direct linkage | " |
| 60 | " | $-O-\bigcirc$ | $F_1$ | " | " | " |
| 61 | " | " | $F_2$ | $\underset{\underset{-CH-CH_2-}{\mid}}{CH_3}$ | " | " |
| 62 | " | " | $F_4$ | " | $-CH_2-$ | " |
| 63 | " | $-OC_3H_7$ | $F_1$ | $\underset{\underset{-CH-CH_2-}{\mid}}{C_2H_5}$ | direct linkage | " |

The following Table 2 shows the structural composition of further dyes which can be produced in accordance with the procedures of Examples 1 to 4. These dyes are of formula

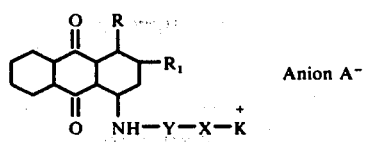

Anion A⁻ where R, R₁, X, Y and K⁺ have the meanings assigned to them in the table. The anion A⁻ may be any one of those named in the specification. The K⁺ symbol may stand for any one of the radicals $K_1$ to $K_{11}$ listed in Table (b). These groupings can be exchanged for another of the given groupings in any particular dye.

Table (b)

| $K_1$ | represents | $-N(CH_3)_3]^+$ |
|---|---|---|
| $K_2$ | " | $-N(C_2H_5)_3]^+$ |

Table (b)-continued

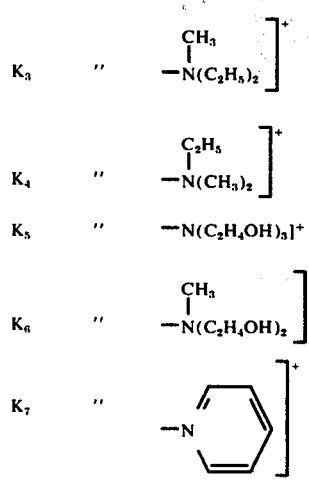

| | | |
|---|---|---|
| K$_3$ | " | $-N(C_2H_5)_2$ with CH$_3$ [+] |
| K$_4$ | " | $-N(CH_3)_2$ with C$_2$H$_5$ [+] |
| K$_5$ | " | $-N(C_2H_4OH)_3]^+$ |
| K$_6$ | " | $-N(C_2H_4OH)_2$ with CH$_3$ [+] |
| K$_7$ | " | pyridinium [+] |

Table (b)-continued

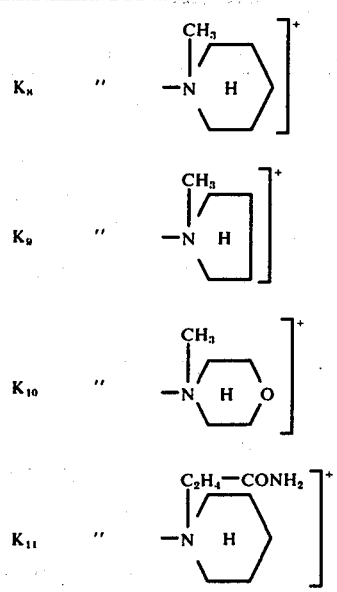

| | | |
|---|---|---|
| K$_8$ | " | N-methylpiperidinium [+] |
| K$_9$ | " | N-methylpyrrolidinium [+] |
| K$_{10}$ | " | N-methylmorpholinium [+] |
| K$_{11}$ | " | N-(C$_2$H$_4$CONH$_2$)-piperidinium [+] |

Table 2

| Example No | R | R$_1$ | K | Y | X | Shade of dyeing on Polyacrylonitrile fibre |
|---|---|---|---|---|---|---|
| 64 | OH | Cl | K$_1$ | $-\overset{CH_3}{\underset{|}{CH}}-CH_2-$ | direct linkage | red violet |
| 65 | " | Br | K$_3$ | " | " | " |
| 66 | " | " | K$_1$ | —⟨H⟩— | " | violet |
| 67 | " | " | K$_3$ | $-\overset{CH_3}{\underset{|}{CH}}-CH_2-$ | $-CH_2-$ | " |
| 68 | NHCH$_3$ | " | K$_1$ | " | " | greenish blue |
| 69 | NH$_2$ | CH$_3$ | K$_1$ | " | " | reddish blue |
| 70 | " | " | K$_2$ | " | $-CH_2-CH_2-$ | " |
| 71 | " | " | K$_3$ | " | $-OCH_2-CH_2-$ | " |
| 72 | " | " | K$_4$ | $-\overset{C_2H_5}{\underset{|}{CH}}-CH_2-$ | direct linkage | " |
| 73 | " | " | K$_5$ | $-\overset{CH_2-\text{cyclohexyl}}{\underset{|}{CH}}-CH_2-$ | " | " |
| 74 | " | " | K$_3$ | —⟨H⟩— | " | " |
| 75 | " | " | K$_1$ | " | " | " |
| 76 | " | CN | K$_1$ | $-\overset{CH_3}{\underset{|}{CH}}-CH_2-$ | $-CH_2-CH_2-$ | blue |
| 77 | " | " | K$_2$ | " | " | " |
| 78 | " | " | K$_3$ | " | $-OCH_2-CH_2-$ | " |
| 79 | " | Cl | K$_1$ | " | " | " |
| 80 | " | " | K$_3$ | " | " | " |
| 81 | " | Br | " | " | direct linkage | " |
| 82 | " | " | K$_4$ | " | " | " |

Table 2-continued

| Example No | R | R₁ | K | Y | X | Shade of dyeing on Polyacrylonitrile fibre |
|---|---|---|---|---|---|---|
| 83 | " | " | $K_1$ | " | $-CH_2-$ | " |
| 84 | " | " | $K_3$ | " | " | " |
| 85 | " | " | $K_4$ | " | " | " |
| 86 | " | " | $K_5$ | " | " | " |
| 87 | " | " | $K_6$ | " | " | " |
| 88 | " | " | $K_7$ | " | " | " |
| 89 | " | " | $K_8$ | " | " | " |
| 90 | " | " | $K_9$ | " | " | " |
| 91 | " | " | $K_{10}$ | " | " | " |
| 92 | " | " | $K_{11}$ | " | " | " |
| 93 | " | " | $K_2$ | " | $-CH_2-CH_2-$ | " |
| 94 | " | " | $K_3$ | " | " | " |
| 95 | " | " | $K_2$ | " | $-OCH_2-CH_2-$ | " |
| 96 | " | " | $K_3$ | " | " | " |
| 97 | " | " | $K_4$ | " | " | " |
| 98 | " | " | $K_{10}$ | " | " | " |
| 99 | " | " | $K_1$ | $\underset{-CH-CH_2-}{\overset{C_2H_5}{\|}}$ | $-CH_2-$ | " |
| 100 | " | " | $K_3$ | " | direct linkage | reddish blue |
| 101 | " | " | $K_7$ | " | " | " |
| 102 | " | " | $K_1$ | $\underset{-CH-CH_2-}{\overset{C_3H_7}{\|}}$ | " | " |
| 103 | " | " | $K_3$ | " | $-CH_2-$ | blue |
| 104 | " | " | $K_1$ | $\underset{-CH-CH_2-}{\overset{CH_2-C_6H_{11}}{\|}}$ | " | " |
| 105 | " | " | $K_3$ | " | " | " |
| 106 | " | " | $K_7$ | " | " | " |
| 107 | " | " | $K_2$ | $\underset{-CH-CH_2-}{\overset{C_2H_4-C_6H_{11}}{\|}}$ | " | " |
| 108 | " | " | $K_1$ | $-C_6H_{11}-$ | direct linkage | " |
| 109 | " | " | $K_2$ | " | " | " |
| 110 | " | " | $K_3$ | " | " | " |
| 111 | " | $-OC_2H_5$ | $K_1$ | " | " | violet |
| 112 | " | " | $K_2$ | " | " | " |
| 113 | " | $-OC_3H_7$ | $K_1$ | " | " | " |
| 114 | " | " | $K_4$ | " | " | " |
| 115 | " | $-O-C_6H_{11}$ | $K_1$ | " | " | " |
| 116 | " | " | $K_4$ | " | " | " |
| 117 | " | " | $K_1$ | $\underset{-CH-CH_2-}{\overset{CH_3}{\|}}$ | $-CH_2-$ | " |

Table 2-continued

| Example No | R | $R_1$ | K | Y | X | Shade of dyeing on Polyacrylonitrile fibre |
|---|---|---|---|---|---|---|
| 118 | " | " | $K_2$ | $\underset{\mid}{C_2H_5}$<br>$-CH-CH_2-$ | direct linkage | " |
| 119 | " | $-OCH_3$ | $K_1$ | $\underset{\mid}{CH_3}$<br>$-CH-CH_2-$ | $-OCH_2CH_2-$ | " |
| 120 | " | " | $K_7$ | " | " | " |

Formulae of representative dyes of the foregoing Examples are as follows:

Example 5

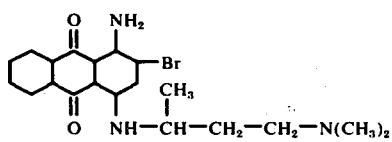

Example 41

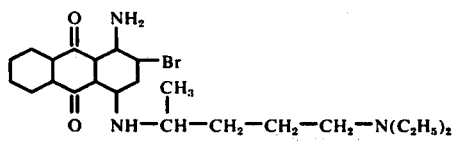

Example 46

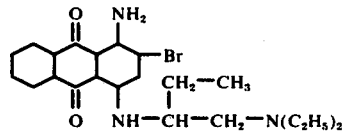

Example 54

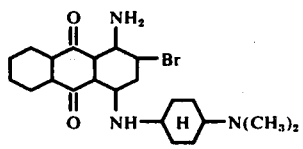

Example 56

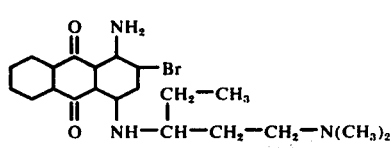

Example 1

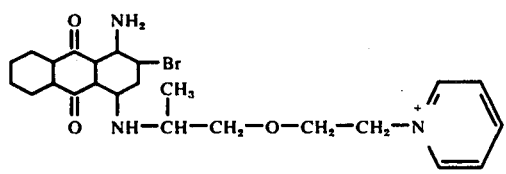

Example 83

-continued

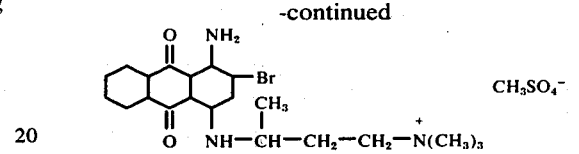

Example 94

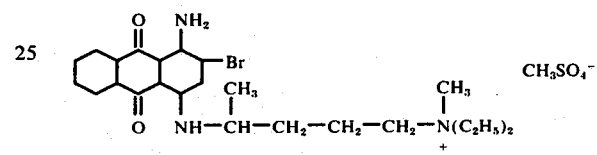

Example 99

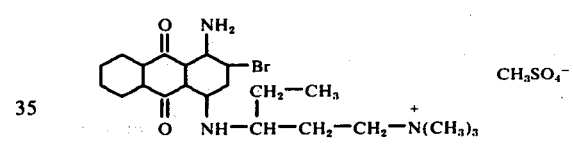

Example 108

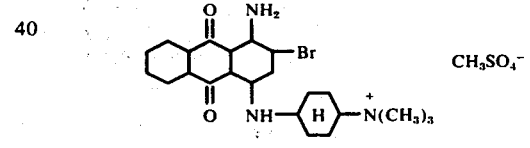

Having thus disclosed the invention what I claim is:
1. A compound of the formula

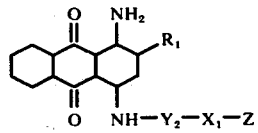

wherein
$R_1$ is chlorine or bromine,
$Y_2$ is

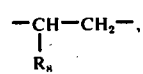

$X_1$ is the direct linkage or $-CH_2-$, $-C_2H_4-$ or $-OC_2H_4-$,
$R_8$ is $-CH_3$, $-C_2H_5$, $-C_3H_7$,

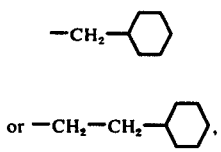

Z is

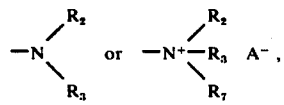

$R_2$ and $R_3$ are, independently, alkyl, cyclohexyl, phenyl, or naphthyl, $R_7$ is alkyl or phenyl, $A^-$ is an anion, and any alkyl group contains 1 to 6 carbon atoms.

2. The basic dye according to claim 1 and of the formula

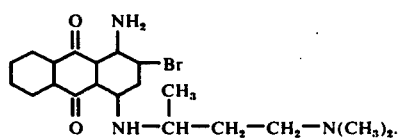

3. The basic dye according to claim 1 and of the formula

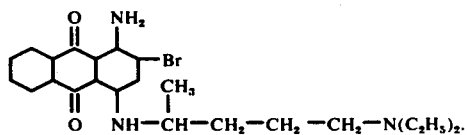

4. The basic dye according to claim 1 and of the formula

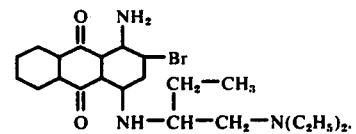

5. The basic dye according to claim 1 and of the formula

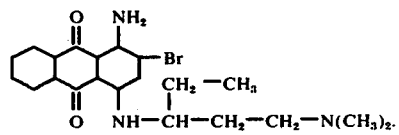

6. The basic dye according to claim 1 and of the formula

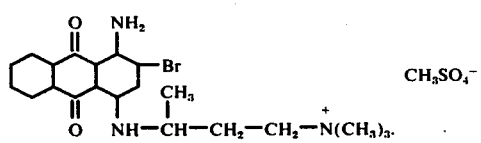

7. The basic dye according to claim 1 and of the formula

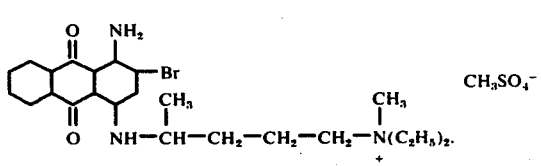

8. The basic dye according to claim 1 and of the formula

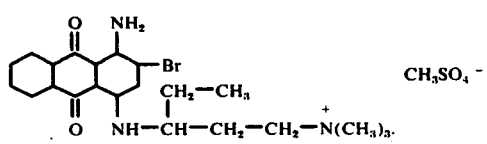

* * * * *